(12) United States Patent
Mackin et al.

(10) Patent No.: US 7,364,539 B2
(45) Date of Patent: Apr. 29, 2008

(54) TELEMETRY SENSING SYSTEM FOR INFANT CARE APPARATUS

(75) Inventors: Michael H. Mackin, Ellicott City, MD (US); Lynn E. Lynam, Bel Air, MD (US)

(73) Assignee: General Electric Company, Schenectady, NY (US)

( * ) Notice: Subject to any disclaimer, the term of this patent is extended or adjusted under 35 U.S.C. 154(b) by 733 days.

(21) Appl. No.: 10/690,149

(22) Filed: Oct. 21, 2003

(65) Prior Publication Data
US 2005/0085687 A1 Apr. 21, 2005

(51) Int. Cl.
*A61G 11/00* (2006.01)
*A61B 7/00* (2006.01)
*A47B 13/00* (2006.01)

(52) U.S. Cl. .............. 600/22; 5/601; 600/587
(58) Field of Classification Search .......... 600/21, 600/22; 5/600, 603; 128/205.26
See application file for complete search history.

(56) References Cited

U.S. PATENT DOCUMENTS

| | | | |
|---|---|---|---|
| 3,638,642 A * | 2/1972 | Heflin, Sr. ........... | 600/301 |
| 3,921,621 A | 11/1975 | Baessler | |
| 3,972,320 A | 8/1976 | Kalman | |
| 4,853,692 A | 8/1989 | Wolk et al. | |
| 5,162,038 A * | 11/1992 | Wilker .............. | 600/22 |
| 5,343,869 A | 9/1994 | Pross et al. | |
| 5,376,761 A * | 12/1994 | Koch et al. ......... | 177/145 |
| 5,748,103 A * | 5/1998 | Flach et al. ........ | 340/870.07 |
| 5,853,005 A | 12/1998 | Scanlon | |
| 5,862,803 A | 1/1999 | Besson et al. | |
| 6,011,477 A | 1/2000 | Teodorescu et al. | |
| 6,200,264 B1 | 3/2001 | Satherly et al. | |
| 6,213,942 B1 | 4/2001 | Flach et al. | |
| 6,215,403 B1 | 4/2001 | Chan et al. | |
| 6,409,654 B1 | 6/2002 | Mc Clain | |
| 2002/0017997 A1 | 2/2002 | Felkowitz | |
| 2002/0044059 A1 * | 4/2002 | Reeder et al. ........ | 340/573.1 |
| 2002/0099277 A1 * | 7/2002 | Harry et al. ......... | 600/301 |
| 2002/0196141 A1 * | 12/2002 | Boone et al. ........ | 340/540 |

FOREIGN PATENT DOCUMENTS

| | | |
|---|---|---|
| DE | 100 43 707 A | 3/2002 |
| EP | 1070479 A | 1/2001 |
| WO | WO 99/04691 | 2/1999 |

* cited by examiner

*Primary Examiner*—Samuel G Gilbert
(74) *Attorney, Agent, or Firm*—Roger M. Rathbun

(57) ABSTRACT

An infant warming apparatus for supporting an infant upon an infant bed. The apparatus has a sensor that is affixed to the skin of the infant to detect one or more physiological functions of the infant. A transmitter is located within the enclosure of the sensor and which transmit the information detected by the physiological sensor to a receiver that is located on the infant care apparatus and which can then convert that information into a recognizable or usable medium. An alternative embodiment includes the transmitter located proximate to the infant within an infant scale located beneath the infant. The sensor is hardwired to the transmitter in the infant scale and signals relating to weight and/or a condition of the infant are transmitted by wireless telemetry to a monitor or other display device to display that information to the caregiver.

1 Claim, 2 Drawing Sheets

TELEMETRY SENSING SYSTEM FOR INFANT CARE APPARATUS

BACKGROUND

The present invention relates to a patient care apparatus and, more particularly, to a wireless communication system that transmits information relating to an infant to a receiver affixed to or integrated within an infant care apparatus.

In the care of newborn infants, there are various types of apparatus that provide heat to an infant and such apparatus can include infant incubators, infant warmers and combinations of the two. In such apparatus, there is normally provided, an infant platform on which the infant is positioned so as to receive the care and that infant platform is a generally planar surface located so as to underlie the infant.

In the case of an infant warmer, there are also normally provided side guards that extend upwardly surrounding the periphery of the infant platform in order to protect the infant and to retain that infant on the infant platform. With an infant incubator, the infant platform is generally surrounded by an enclosure that provides a controlled atmosphere for the infant including control of the heat and humidity within the protective enclosure.

An infant warmer is shown and described in U.S. Pat. No. 5,474,517 of Falk et al as prior art to that patent; a infant incubator is shown and described in U.S. Pat. No. 4,936,824 of Mackin et al and a combination apparatus that combines the functions of both an infant warmer and an infant incubator is shown and described in U.S. Pat. No. 6,224,539 of Jones et al.

A commonality involved in the providing of care to an infant using any of such apparatus is that there are normally present, a number of monitors that determine certain physiological or physical conditions of the infant and those monitors receive the necessary information from the infant by means of sensors that are actually affixed to or are located proximate to the infant. Specifically, such sensors that are normally affixed to the infant include an infant skin temperature sensor that monitors the surface temperature of the skin of the infant and also a standard three lead ECG sensor that senses ECG of the infant as well as respiratory effort by thoracic impedance.

With the infant, therefore, both sensors compete for space on the skin of the infant and both sensors currently have hard wires that connect the sensors to a monitor that displays the particular sensed condition. In addition, of course, there are other sensors that may or may not be actually affixed to the infant but are in close proximity thereto and can include sensors providing information to $SPO_2$ monitors, EEG monitors, security system devices and even a scale to ascertain the weight of the infant.

Obviously, one of the difficulties in having one or more sensors proximate to or affixed to the infant raises issues relating to the access to the infant since the caregiver needs, at times, to have full access to the infant and is often hampered by the presence of wires, tubes and the like that are attached to the infant and which make full and unfettered access to the infant somewhat difficult. In addition, the infant may be moved on the infant platform or rolled over by the caregiver during the process of caring for the infant or carrying out some intervention on the infant and, again, the presence of wires leading to sensors affixed to the infant creates problems.

With the vast myriad of wires, there is also the possibility that one or more of the wires may inadvertently become disconnected and may go unnoticed or, if noticed, require the caregiver to reattach that sensor, thereby causing a disruption to the infant who is already at a time of great stress.

It would therefore be advantageous to have a system in place that operates with an infant care apparatus that transmits signals from various infant probes and sensors or other information gathering devices, that must be in close proximity to the infant or attached to that infant, by some wireless telemetry means to a visual display or other information providing device that is affixed to or is integrated into the infant care apparatus.

SUMMARY OF THE INVENTION

Accordingly, the present invention relates to an infant care apparatus, such as an infant warmer that has a wireless transmitting system that can transmit signals representative of data or information relative to the infant being cared for in the apparatus to some recognition receiver or monitor that can recognize and use that information in a useful manner for the caregiver.

As will be seen, the present invention is shown and described herein with respect to an infant care apparatus wherein an infant is provided with heat to assist in the well being of that infant, however, the present invention is also applicable to other types of patient care apparatus where a patient is undergoing some type of therapy or treatment by the apparatus and where one or more sensors are used to assess the state of the patient.

In any event, the infant care apparatus of the present invention has a base with an infant platform on which the infant is positioned and, with the foregoing explanation as to other types of patient apparatus, there are certain types of infant care apparatus that are preferred for use with the invention, that is, an infant incubator where the infant is basically enclosed within a protective environment with controlled heat and humidity, an infant warmer where the infant is lying in a more open environment and heated by an overhead radiant heater or a combination of the two apparatus, where the apparatus itself can be converted between a status where it functions as an infant warmer and a status where it functions as an infant incubator.

With the infant apparatus of the present invention, therefore, there are one or more sensors that are generally affixed to the infant and which are used to obtain information and data concerning the status of the infant. The sensor or sensors produce an electrical signal that is transmitted by means of a wireless transmitting system to a receiving apparatus. That information can then be channeled by the receiving apparatus for a variety of uses, including sending the information to a monitor affixed to or integral with the infant apparatus where there is a visual display of the particular sensed condition of the infant.

In one embodiment, the standard three lead ECG sensor is combined with a temperature sensor, such as a thermistor, so that only one sensor need be affixed to the infant and yet provide information as to both functions. That sensor also includes the transmitter to send that combined information on to the receiving apparatus that is physically located on the infant care apparatus. The receiving apparatus can, in turn, send that information on to a visual display to be seen by the caregiver and/or to other various uses and functions.

With that combined sensor, the single sensor can, therefore, transmit thermal data to the control system of the heater for the infant care apparatus so that the information relating to the infant skin temperature can be used in a heating algorithm, as is conventional, to control the power to the heater. In addition, the same combined sensor can be used to transmit ECG information and data as well as transmit respiration impedance data to a multi-parameter monitor.

Thus, transmission of the electronic signals from the sensor or sensors is carried out by means of a transmitter located in the sensor itself as a part thereof such that there are no hard wires that carry signals from the various sensors to the receiving apparatus mounted on or incorporated into the infant care apparatus and, accordingly, the infant is more accessible and the vast myriad of wires associated with the infant care apparatus are eliminated. Due to the relatively short distance over which the wireless transmission takes place, the transmitter can be a low power device and miniaturized so as to be incorporated into the sensor itself.

As an alternative embodiment, the transmitter may be located in some area that is proximate to the infant, that is, the transmitter can be located directly beneath the infant and may be hardwired to the sensor or sensors that are affixed to the infant. By such arrangement, the transmitter can thereby receive signals from the sensor or sensor by the hard wires and thereafter transmit those signals via wireless telemetry to the receiving apparatus that is located on the infant care apparatus.

That transmitter can, therefore, be separately mounted within the infant care apparatus or may be incorporated into a further piece of equipment, such as the infant scale, so that the transmitter can not only send the signals from sensors on or proximate to the infant but can also receive and transmit the signals representative of the weight of the infant to the receiving apparatus that can provide those signals to a visual display so that the weight of the infant is displayed on a visual monitor to the caregiver as well as the infant conditions determined by the sensor(s).

With either embodiment, the receiving apparatus located on the infant care apparatus that receives the wireless signals can also be associated with a further transmitter so that those signals that originate from a sensor affixed to or proximate to the infant can be retransmitted to some central file or location where that information can be retained to maintain a current source of information relating to the infant under care in the infant care apparatus.

These and other features and advantages of the present invention will become more readily apparent during the following detailed description taken in conjunction with the drawings herein.

DETAILED DESCRIPTION OF THE INVENTION

Figure 1:
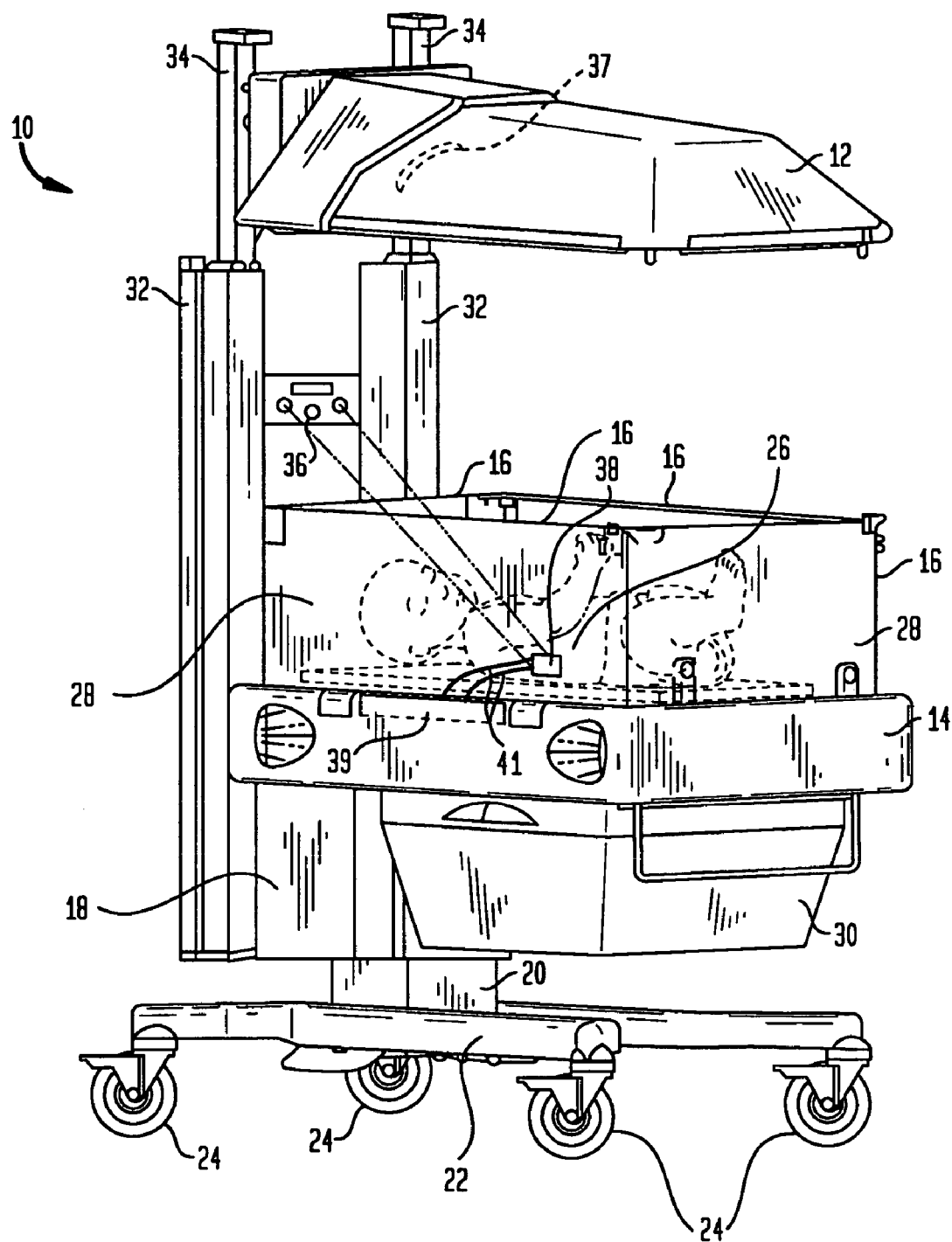
FIG. 1 of a perspective view of an infant warming apparatus having a wireless communication system in accordance with the present invention.

Referring now to FIG. 1, there is shown a perspective view illustrating the present invention and showing an infant care apparatus 10 constructed in accordance with the present invention. Although the invention is shown and described specifically in relation to an infant care apparatus such as a infant warmer, it will be seen that the present invention can be applicable to other types of patient care apparatus, including other types of infant care apparatus, and still carry out the purposes of the present invention.

In FIG. 1, therefore, the infant care apparatus 10 includes a canopy 12 shown in its upper position. The infant care apparatus 10 illustrated can function both as an incubator when the canopy 12 is in a lower position and an infant warmer when the canopy 12 is in its upper position as shown in FIG. 1.

The apparatus itself can be of the type that is shown and described in U.S. Pat. No. 6,231,499 of Jones entitled LIFT MECHANISM FOR INFANT CARE APPARATUS CANOPY and U.S. Pat. No. 6,585,636 of Jones et al and entitled HEATER DOOR MECHANISM FOR INFANT WARMING APPARATUS, and the disclosures of those U.S. Patents are hereby incorporated herein by reference in their entirety.

As shown, the infant care apparatus 10 includes an infant platform 14 that underlies and supports an infant resting on an infant bed 15. As is also seen, a plurality of walls 16 are provided to contain the infant safely within the infant care apparatus 10 and are located at all of the four sides of the infant platform 14. The walls 16 are preferable constructed of transparent plastic material and, as will be explained, cooperate with other components in order to provide an incubator function to the infant care apparatus 10 when the infant care apparatus 10 is functioning as an incubator.

The infant platform 14 is mounted to a moveable vertical base member 18 which, in the preferred embodiment, is movably affixed to a stationary vertical base member 20, which, in turn, is mounted to a base 22 having wheels 24 for ready movement of the infant care apparatus 10.

The vertical movable base member 18 is preferably mounted so that the user can adjust the height of the infant platform 14 by raising and lowering the movable vertical member 18 as desired, thus the infant platform 14 can be adjusted to the preferred height by the user. As further standard features, the walls may have handholes (not shown) to afford access to the infant 26 when in the incubator configuration and which generally have doors 28 that can be opened to obtain access to the infant 26 and, of course, closed when the particular intervention has been completed to preserve the desired environment surrounding the infant.

Another convenient feature includes a drawer 30 to retain supplies or other devices needed to carry out some operation on the infant and which is normally located beneath the infant platform 14. Other features include the maneuverability of the walls 16 that are pivotally mounted at their bases to the infant platform 14 such that the doors can be swung outwardly and downwardly and, as a further alternative, can be easily fully removed from the infant platform 14. As such, therefore, when the canopy 12 of the infant warming apparatus 10 is in its upper position as shown in FIG. 1, the walls 16 can be dropped downwardly or removed altogether so that the attending personnel can have unlimited access to an infant resting on the infant platform 14 to perform interventions on that infant.

Further structural components of the infant warming apparatus 10 include stationary frame members 32 that are affixed to the base member 18 and, as shown, there are two vertical stationary frame members 32 in the preferred embodiment although there may be only one or there may be further numbers of such members. Two vertical movable frame members 34 are movably fitted into the stationary frame members 32 and which can be moved upwardly and downwardly by the user in converting the infant care apparatus 10 between its function as an incubator and its function as an infant warmer.

A control module 36 is conveniently positioned intermediate the stationary frame members 32 and may include displays of various monitored parameters as well as include the various controls for operation of the functions of the infant warming apparatus 10.

As may now be seen in general, in the operation of the infant warming apparatus 10, the canopy 12, in the preferred embodiment, houses a radiant heater 37. The canopy 12 can be moved between its upper position, as shown in FIG. 1, wherein the infant care apparatus acts as an infant warmer and a lower position wherein the infant care apparatus acts as an infant incubator where the infant 26 is provided with warm air and controlled humidity in the normal functioning of an incubator.

As also can be seen in FIG. 1 there is a sensor 38 that is affixed to the skin of the infant 26 to obtain data and information and to transmit the data and information via a wireless means to the infant care apparatus 10 where that data and information is received and interpreted as will later be explained. As such, the sensor 38 includes a transmitter and there is a receiver located on the infant care apparatus 10 which may be located in the control module 36 as will be later explained.

As a further embodiment, there is also shown an infant scale 39 that is, as is conventional, located beneath the infant. The infant scale 39 is, of course used to weigh the infant resting on the infant bed 15 and the infant scale 39 itself can be constructed and used as shown and described in U.S. Pat. No. 5,376,761, issued Dec. 27, 1994 of Christopher Dykes and entitled "In Bed Infant Scale".

In FIG. 1, there can be seen hard wires 41 that extend from the sensor 38 to the infant scale 39 so as to transmit signals from the sensor 38 to a transmitter (not shown) that can be located proximate to the infant 26 and, as one possible location, the transmitter can actually be incorporated into the infant scale 39 itself. Accordingly, the transmitter can be used to transmit signals from the sensor 38 that are received by the hard wires 41 to a receiver that is located in the control module 36 where the information from the signals can be displayed to the caregiver or sent to a further location.

In addition, the signals that are provided by the infant scale 39 indicative of the weight of the infant 26 can also be sent via the wireless telemetry to the receiver in the control module 36 so that the same transmitter can be used both to provide visual information as to the weight of the infant 26 to the caregiver at the control module 36 as well as transmit whatever infant condition is being sensed by the sensor 38.

Figure 2:
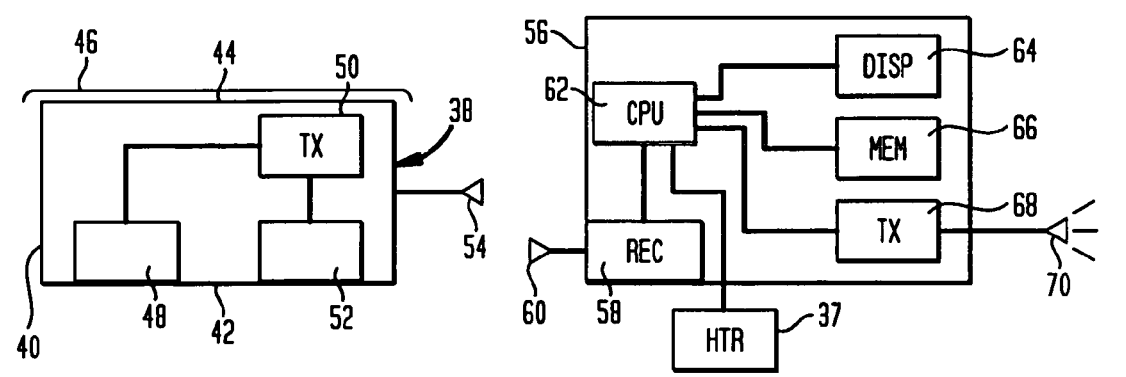
FIG. 2 is a block diagram of the components used in carrying out the present invention.

Turning now to FIG. 2, taken along with FIG. 1, there is shown a block diagram of the various components used with one embodiment of the present invention. As can be seen, the sensor 38 comprises an enclosure 40 and which is adapted to be affixed to the skin of an infant. Thus, there may be a contact side 42 that is actually affixed in contact with the skin of the infant and an outer side 44 that may be covered with a heat reflecting foil 46 to protect the sensor 38 from the effects of heat from, for example, the radiant heater 37 that is maintaining the infant 26 at a desired temperature. A hydrogel, not shown, is normally used to provide a patient interface between the contact side 42 and the skin of the infant.

Also contained within the enclosure 40 is a three lead ECG sensing element 48 that reads the ECG of the infant and sends the electronic signal containing that information to a transmitter 50 within the enclosure 40. Additionally, there is a temperature sensing element 52, such as a thermistor, within the enclosure 40 and which senses the skin temperature of the infant and sends an electronic signal with that information to the transmitter 50.

As such, the sensor 38 contains the ECG sensing element 48 and the temperature sensing element 52, both of which gather the respective information from the infant and send the information to the transmitter 50 which transmits the information by wireless means via the antenna 54 to the receiving apparatus 56 that is located on the infant care apparatus 10 and, preferably, within the control module 36.

Since the signals traveling through the wireless communication system from the transmitter 50 to the receiving apparatus 56 only travel a relatively short distance, that is, from the sensor 38 affixed to the infant to the receiving apparatus 56 that is attached to or integrated into the infant care apparatus 10, the power of the transmitter can be extremely small. In effect, the transmitter can be a consumable device with a fixed life internal power source. The communication protocol can be a number of existing protocols, including Bluetooth, WiFi or a custom protocol.

The transmitter 50 and receiving apparatus 56 can be coded to a specific frequency so that the receiving apparatus 56 is able to discern that the information has been received with respect to a particular infant and not from another infant in the vicinity so that it is assured that only the correct information is inputted to the receiving apparatus 56. The security of the information is important inasmuch as, in one embodiment, the skin temperature of the infant is used to control the power to the heater used to heat the infant.

As shown, the sensor 38 includes ECG sensing and temperature sensing, however, there may be other sensing elements that act in conjunction with a transmitter to transmit the information relating to the infant by wireless telemetry to the receiving apparatus 56 located on the infant care apparatus 10. For example, the infant's weight may be sensed by the scale located underneath the infant bed 15 to transmit information regarding the weight of the infant via the present wireless system to a visual read out viewable by the caregiver and located on the infant care apparatus 10.

In the event the sensor 38 monitors the vital signs of an infant, those signals can also be sent by means of the present wireless system to a vital signs monitor mounted to or incorporated into the infant care apparatus 10. Other information relating to the infant that may be sensed by a sensor and transmitted by the present wireless system can include blood pressure, blood gas or may include an internal hospital security system that would alert the hospital in the event the infant were moved to a location outside of a defined secure location.

The receiving apparatus 56 is illustrated in FIG. 2 as being within a single block for illustration purposes only, since any one or more of the components to be described with respect to the receiving apparatus 56 may be located in separate areas of the infant care apparatus 10, however, it is convenient for all of the components making up the receiving apparatus to be located in the control module 36.

Thus, the receiving apparatus 56 comprises a receiver 58 that receives the electronic signals from the transmitter 50 by means of antenna 60 and therefore receives the information sensed in the infant 26 by the sensor 38. That information is processed by a CPU 62 and thereafter may be sent to a monitor display 64 so that the information can be visually perceived by the caregiver and/or stored in memory 66 for later use such as for trending. As a further alternative embodiment, the information can be communicated to a further re-transmitter 68 and then transmitted, through the antenna 70 to a central station within a hospital where that data and information can be collected and stored and/or visually monitored.

As a still further alternative embodiment, the information that is transmitted from the sensor 38 to the receiving apparatus 56 can be used by the CPU 62 as an input into a controller of the heating algorithm such that the intensity of the output of the heater 37 is varied depending upon the skin temperature of the infant 26 much the same as in the prior art but using the wireless telemetry of the present invention to eliminate the prior hard wires that were heretofore necessary to send the signal indicative of the infant skin temperature to the controller of the infant care apparatus 10.

Figure 3:
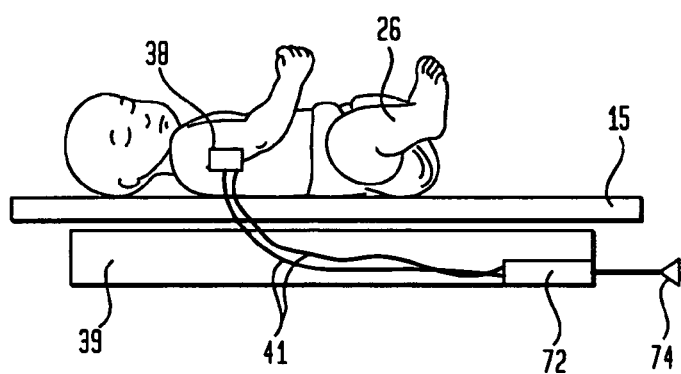
FIG. 3 is a block diagram illustrating an alternative embodiment of the present invention.

Turning finally to FIG. 3, there is shown a block diagram of an embodiment of the present invention where there is an infant scale 39 that is located beneath the infant bed 15 on which the infant 26 rests. As such, the infant scale 39 can measure the weight of the infant 26 resting on that infant bed 15. There is a transmitter 72 that is located proximate to the infant bed 15, and the infant 26, preferably beneath the infant bed 15 within platform 14, that can receive signals from the sensor 38 affixed to the infant 26 by means of hard wires 41.

As shown, one location of the transmitter 72 is actually incorporated into the infant scale 39 such that the transmitter 72 can transmit, by means of the antenna 74, signals that are received from the sensor 38 representing some condition of the infant 26, and/or signals from the infant scale 39 by wireless telemetry. Certainly one advantage of the embodiment where the transmitter 72 is proximate to the infant platform 14 but not incorporated into the sensor 38 is that there is sufficient power available to the transmitter 72 and it need not be battery operated but can operate off the power available in the infant care apparatus 10 or the infant scale 39 and the transmitter 72 can thus be a more powerful transmitter carrying a further distance.

The receiving apparatus with the FIG. 3 embodiment can be the same as is used in the FIG. 2 embodiment. Therefore, in this embodiment, the caregiver can be provided with information as to the weight of the infant by some visual display located at or near the control module 36 of FIG. 1 as well as one or more conditions sensed in the infant 26.

Those skilled in the art will readily recognize numerous adaptations and modifications which can be made to the infant care apparatus of the present invention which will result in an improved telemetry system for an infant care apparatus, yet all of which will fall within the scope and spirit of the present invention as defined in the following claims. Accordingly, the invention is to be limited only by the following claims and their equivalents.

We claim:

1. A patient care apparatus, said patient care apparatus comprising a base having a bed on which a patient is adapted to be positioned, a scale located beneath the bed to measure the weight of a patient resting on the bed, at least one sensor adapted to be affixed to or located in close proximity to a patient to sense data related to a patient and to produce signals representative of that data, a wireless transmitter located in said scale in close proximity to a patient and adapted to receive the signals from the at least one sensor and to transmit those signals by a wireless means, the patient care apparatus having a receiver adapted to receive the signals from said transmitter and to convert said signals into a form recognizable by a caregiver as indicative of the sensed data of a patient.

* * * * *